US008280748B2

(12) United States Patent
Allen et al.

(10) Patent No.: US 8,280,748 B2
(45) Date of Patent: Oct. 2, 2012

(54) BED MANAGEMENT

(75) Inventors: James M. Allen, Batesville, IN (US);
Williams F. Collins, Columbus, IN (US); Keith A. Huster, Sunman, IN (US); Carl W Riley, Milan, IN (US);
Patricia A Glidewell, Apex, NC (US)

(73) Assignee: Hill-Rom Services, Inc., Batesville, IN (US)

(*) Notice: Subject to any disclaimer, the term of this patent is extended or adjusted under 35 U.S.C. 154(b) by 594 days.

(21) Appl. No.: 11/869,069

(22) Filed: Oct. 9, 2007

(65) Prior Publication Data
US 2008/0109255 A1 May 8, 2008

Related U.S. Application Data

(60) Provisional application No. 60/862,223, filed on Oct. 20, 2006.

(51) Int. Cl.
*G06Q 50/00* (2006.01)
*G06Q 10/00* (2006.01)
*A47B 71/00* (2006.01)

(52) U.S. Cl. ................... 705/2; 705/7.12; 5/600

(58) Field of Classification Search ............... None
See application file for complete search history.

(56) References Cited

U.S. PATENT DOCUMENTS

| 4,135,241 | A | 1/1979 | Stanis et al. |
|---|---|---|---|
| 5,561,412 | A | 10/1996 | Novak et al. |
| 5,699,038 | A | 12/1997 | Ulrich et al. |
| 5,760,704 | A | 6/1998 | Barton et al. |
| 5,867,821 | A | 2/1999 | Battantyne et al. |
| 5,924,074 | A * | 7/1999 | Evans ................. 705/3 |
| 5,991,730 | A | 11/1999 | Lubin et al. |
| 5,995,937 | A | 11/1999 | DeBusk et al. |
| 6,147,592 | A | 11/2000 | Ulrich et al. |
| 6,211,790 | B1 | 4/2001 | Radomsky et al. |
| 6,356,874 | B1 | 3/2002 | Øhrn |
| 6,362,725 | B1 | 3/2002 | Ulrich et al. |
| 6,897,780 | B2 | 5/2005 | Ulrich et al. |
| 7,092,376 | B2 | 8/2006 | Schuman |
| 7,242,308 | B2 | 7/2007 | Ulrich et al. |

(Continued)

OTHER PUBLICATIONS

Josh Silvers, & Al Wiggs. (Jul. 2005). "Behind the trend toward purchasing versus renting." Nursing Homes, 54(7), pp. 14-15. (Retrieved Jun. 9, 2012, from ABI/INFORM Global.*

(Continued)

*Primary Examiner* — Luke Gilligan
*Assistant Examiner* — Rachel L Porter
(74) *Attorney, Agent, or Firm* — Barnes & Thornburg LLP

(57) ABSTRACT

A computing device, system, method and machine readable medium for managing beds of a healthcare facility is provided. A system includes a client device and a server computing device. The client device may generate a request to assign a bed to a patient, present a list of beds to assign the patient, and receive a selection that identifies a bed of the list of beds. The server computing device may generate the list of beds presented by the client device in response to the request. The server computing device may retrieve an electronic medical record for the patient, and obtain healthcare attributes for the patient from the electronic medical record. The server computing device may generate the list based upon capabilities of a plurality of beds and the healthcare attributes of the patient retrieved from the electronic medical record. The server computing device may further assign to the patient the bed identified by the selection.

10 Claims, 4 Drawing Sheets

U.S. PATENT DOCUMENTS

| | | |
|---|---|---|
| 7,263,501 B2 | 8/2007 | Tirinato et al. |
| 7,315,535 B2 | 1/2008 | Schuman |
| 7,319,386 B2 | 1/2008 | Collins, Jr. et al. |
| 2001/0050610 A1 | 12/2001 | Gelston |
| 2002/0158919 A1 | 10/2002 | Nacey |
| 2003/0074222 A1 | 4/2003 | Rosow et al. |
| 2003/0078810 A1 | 4/2003 | Cole et al. |
| 2003/0078811 A1 | 4/2003 | Cole et al. |
| 2003/0195838 A1* | 10/2003 | Henley .......................... 705/37 |
| 2004/0128168 A1 | 7/2004 | Wyatt |
| 2004/0243446 A1 | 12/2004 | Wyatt |
| 2005/0010441 A1 | 1/2005 | Wheeler |
| 2005/0071198 A1 | 3/2005 | Krupa |
| 2005/0219059 A1 | 10/2005 | Ulrich et al. |
| 2006/0114888 A1 | 6/2006 | Schuman |
| 2006/0247948 A1 | 11/2006 | Ellis et al. |
| 2007/0129983 A1 | 6/2007 | Scherpbier et al. |
| 2008/0027754 A1 | 1/2008 | Auker et al. |
| 2008/0065434 A1* | 3/2008 | Rosow et al. .................... 705/5 |

OTHER PUBLICATIONS

"COMposer™ Communication System Service Manual", by Hill-Rom Services, Inc., (2003).

"COMLinx™ Enterprise Solutions, Nurse Communication Module, User's Guide", by Hill-Rom Services, Inc., (2000).

* cited by examiner

BED MANAGEMENT

This application claims the benefit, under 35 U.S.C. §119(e), of U.S. Provisional Application No. 60/862,223 which was filed Oct. 20, 2006 and which is hereby incorporated by reference herein.

BACKGROUND

The present disclosure relates to systems and methods for managing resources, and particularly, to systems and methods for managing bed assignments in a healthcare facility.

Beds used in a healthcare environment have capabilities that address healthcare needs and/or medical conditions of a patient. However, pairing patients with suitable beds requires an intimate understanding of the capabilities of each bed, as well as, how such capabilities relate to healthcare needs and conditions of patients. Given the large number of bed models available to hospitals and given many bed models have a large number of optional capabilities, determining exactly which bed is "best" or a "good fit" for a given patient's needs can be a daunting task.

To make matters even more difficult, pairing of patients with beds is also dependent upon bed availability. A caregiver may prefer to assign a bed of first class to a patient due to the patient having a particular healthcare need. All beds of the first class, however, may be currently occupied or otherwise unavailable. An available bed of a second class may have similar attributes to beds of the first class and thus be suitable for the patient. Unless the caregiver is aware of the interchangeability of the beds in these two bed classes in regard to the healthcare need of the patient, the caregiver may assign a less suitable bed of a different class to the patient and/or needlessly rent another bed of the first bed class from a third party distributor in order to accommodate the healthcare need of the patient.

SUMMARY

A method, computing device, system and/or machine-readable medium for assigning a bed to a patient is provided and comprises one or more of the features recited in the appended claims and/or the following features which, alone or in any combination, may comprise patentable subject matter:

A machine readable medium for managing beds includes a plurality of instructions. The instructions of the machine readable medium, in response to being executed, result in a computing device receiving patient data that identifies a plurality of healthcare attributes of a patient, and assigning a bed to the patient based upon the plurality of healthcare attributes of the patient identified by the patient data and a capability of the bed. Execution of the instructions may further result in the computing device receiving a request to assign a bed to the patient, and assigning the bed to the patient in response to the request. The instructions, in response to being executed, may also result in the computing device selecting the bed based upon at least one healthcare attribute of the plurality healthcare attributes identified by the patient data. The patient data may include a healthcare code that identifies a medical condition as one of the healthcare attributes of the patient. The healthcare code may also identify a medical procedure as one of the healthcare attributes of the patient.

The computing device in response to executing the instructions may identify one or more beds or one or more unassigned beds that address a healthcare attribute of the plurality of healthcare attributes, present the one or more beds to a user, and receive a selection from the user that identifies the bed of the one or more beds to be assigned to the patient. The assigning may also include identifying one or more unassigned beds with a capability that addresses at least one healthcare attribute of the patient as identified by the patient data.

The instructions in response to being executed may result in the computing device ranking unassigned beds based upon whether capabilities of the unassigned beds are suitable for the plurality of healthcare attributes identified by the patient data and presenting a ranking of one or more beds of the unassigned beds to a user. The instruction may further result in receiving a selection from the user that identifies the bed of the one or more beds to be assigned to the patient.

Execution of the instructions may also result in the computing device ranking unassigned beds of the healthcare facility and a bed distribution facility based upon suitability of the unassigned beds for the plurality of healthcare attributes identified by the patient data. The execution may also result in receiving a selection from the user that identifies a bed of the bed distribution facility as the bed to be assigned to the patient, and placing an order for the bed of the bed distribution facility.

The instructions may also result in defining bed classes based upon bed capabilities and ranking bed classes based upon suitability of beds of the bed classes for the plurality of healthcare attributes identified by the patient data.

A computing device to manage beds of a healthcare facility may include a data storage device and a processor operatively coupled to the data storage device. The data storage device may include instructions, and the processor may execute the instructions. In response to executing the instructions, the processor may receive an electronic medical record that identifies healthcare attributes of a patient. The electronic medical record may include a healthcare code that identifies at least one healthcare attribute of the patient. The processor may further determine suitability of a bed for the patient based upon capabilities of the bed and the healthcare attributes of the patient identified by the electronic medical record. The processor may also present beds that are ranked based upon capabilities of the beds and the plurality of healthcare attributes identified by the electronic medical record. The processor in determining the suitability of the bed for the patient may determine suitability of each bed of a plurality of beds for the patient based upon bed capabilities and the healthcare attributes of the patient, and may assign a bed of the plurality of beds to a patient based upon suitability of the plurality of beds for the patient.

In determining suitability, the processor may determine suitability of beds of a healthcare facility and beds of a distribution facility for the patient based upon bed capabilities and the plurality of healthcare attributes of the patient, and order a bed of the distribution facility in response to a user selection that identifies a bed of the distribution facility.

A system for managing beds may include a client device and a server computing device. The client device may generate a request to assign a bed to a patient, present a list of beds to assign the patient, and receive a selection that identifies a bed of the list of beds. The server computing device may generate the list of beds presented by the client device in response to the request. The server computing device may retrieve an electronic medical record for the patient, and obtain healthcare attributes for the patient from the electronic medical record. The server computing device may generate the list based upon capabilities of a plurality of beds and the healthcare attributes of the patient retrieved from the electronic medical record. The server computing device may further assign to the patient the bed identified by the selection.

A method for managing beds includes retrieving a medical record for the patient and identifying a plurality of healthcare attributes from the medical record. The method may also include determining suitability of a plurality of beds for a patient based upon capabilities of the beds and the plurality of healthcare attributes of the patient. The method may also include presenting the plurality of beds to a user based upon suitability of the plurality of beds, and assigning a bed to the patient based upon a user selection that identifies the bed from the plurality of beds.

Additional features, which alone or in combination with any other feature(s), including those listed above and those listed in the claims, may comprise patentable subject matter and will become apparent to those skilled in the art upon consideration of the following detailed description.

BRIEF DESCRIPTION

The invention described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

DETAILED DESCRIPTION

In the following description, numerous specific details such as logic implementations, types and interrelationships of system components, and logic partitioning/integration choices are set forth in order to provide a more thorough understanding of the present invention. One skilled in the art, however, appreciates that the invention may be practiced without such specific details. In other instances, control structures, gate level circuits and full instruction sequences have not been shown in detail in order not to obscure the invention.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; and others.

The following description describes techniques for assigning beds to patients based upon capabilities of the beds and healthcare attributes of the patients. The bed management system may allocate a bed to a patient in response to updates regarding the patient's condition or in response to receiving a request to allocate a bed to the patient. For example, a request to allocate a bed to a patient may automatically be generated by an admissions, discharge, and transfer (ADT) system as part of the admissions process. During admissions, information about the patient is gathered and entered into the ADT system. The ADT system may store the received information and/or update other systems based upon the received information. In particular, the ADT system may access a patient workflow system in order to generate a new electronic medical record and/or update an existing electronic medical record for the patient to reflect the medical condition of the patient and/or procedures to be performed for the patient.

The ADT system may further request the bed management system to pair the patient with a bed while taking into account attributes of the patient. The bed management system in response to such a request may determine the healthcare attributes of the patient based upon healthcare codes obtained from the patient's electronic medical record or information maintained by other systems of the facility such as, for example, the ADT system. The bed management system may further identify available beds and their capabilities and assign an available bed to the patient which has capabilities suitable for the healthcare attributes of the patient. Further details and features regarding bed management are present below in regard to the depicted embodiments.

Figure 1:
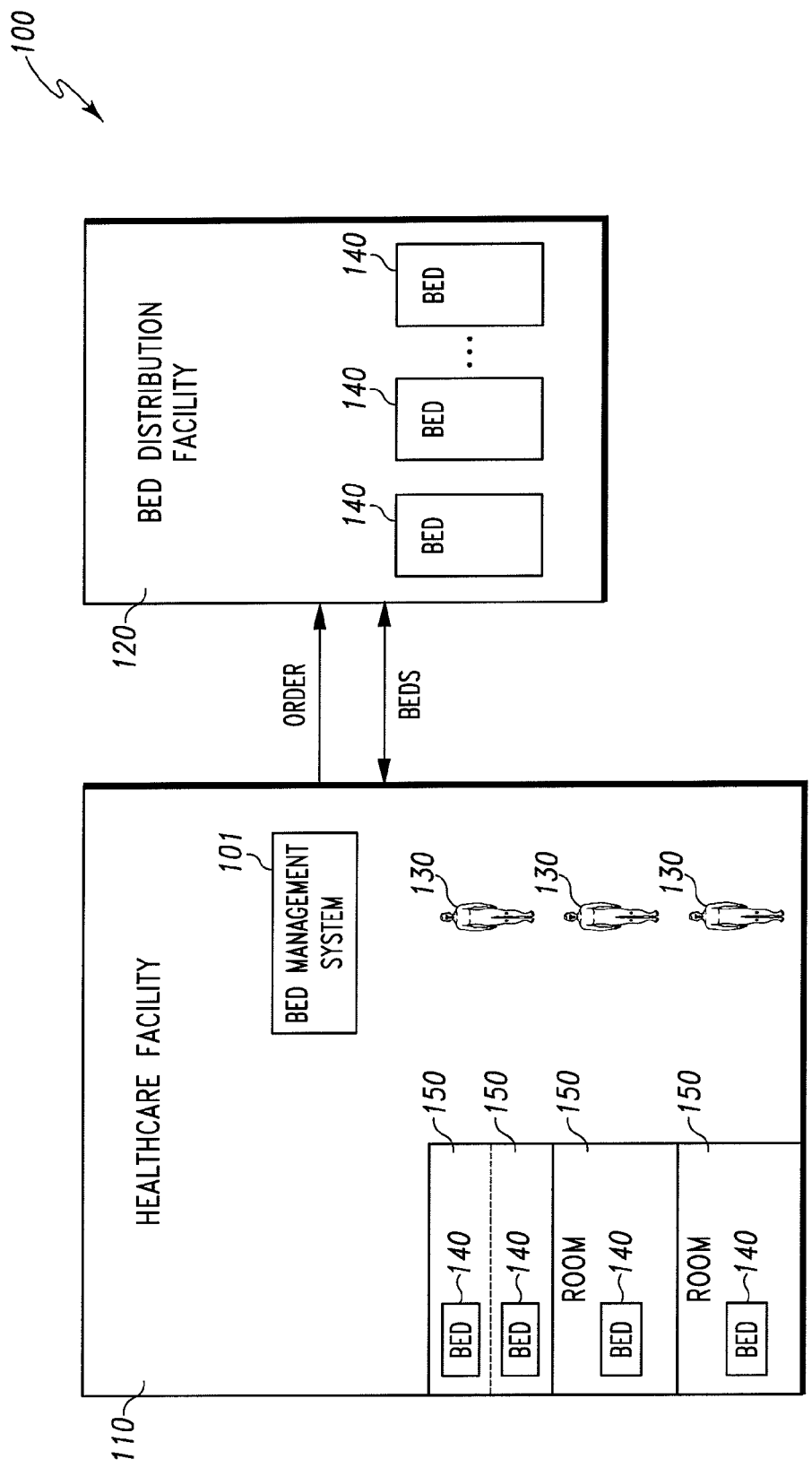
FIG. 1 is a block diagram showing a healthcare environment in which a bed management system manages beds of a healthcare facility and a bed distribution facility.

Referring now to FIG. 1, a healthcare environment 100 is depicted in which a bed management system 101 assigns beds to patients. As depicted, the healthcare environment 100 comprises a healthcare facility 110 and a bed distribution facility 120. While a single healthcare facility 110 and a single bed distribution facility 120 are depicted, multiple healthcare facilities 110 and/or multiple bed distribution facilities 120 are contemplated by the present disclosure. The healthcare facility 110 may correspond to a hospital, health clinic, nursing home, rest home, sanatorium, rehabilitation facility or other facility that cares for physical and/or mental conditions of clientele or patients.

During the course of caring for a patient 130, the bed management system 101 may assign patients 130 to beds 140 and/or beds 140 to patients 130 based upon bed capabilities and patient attributes. The bed management system 101 in one embodiment may indirectly perform such bed assignments by assigning rooms/areas 150 to the patients 130 or patients 130 to rooms/areas 150 based upon capabilities of beds 140 located in such rooms/areas 150. As explained below, the bed management system 101 of the healthcare facility 110 in one embodiment pairs or assists a user in pairing patients 130 with appropriate beds 140 based upon patient attributes such as, for example, physical health conditions, mental health conditions, physical traits, procedures performed, and/or procedures to be preformed and bed capabilities such as, for example, type of mattress, egress features, patient positioning sensors, and the like.

The bed distribution facility 120 may receive orders for beds 140 from the healthcare facility 110 and may sell, lease, consign or otherwise convey the beds 140 to the healthcare facility 110 per received orders. In this manner, the bed distribution facility 120 enables the healthcare facility 110 to maintain a smaller inventory of beds 140 since additional beds 140 or specialty beds 140 with unique capabilities may be acquired from the bed distribution facility 120 on an as needed basis. The bed distribution facility 120 may be a separate corporate entity from the healthcare facility 110;

however, the bed distribution facility 120 may alternatively be owned by or otherwise affiliated with the healthcare facility 110.

Figure 2:
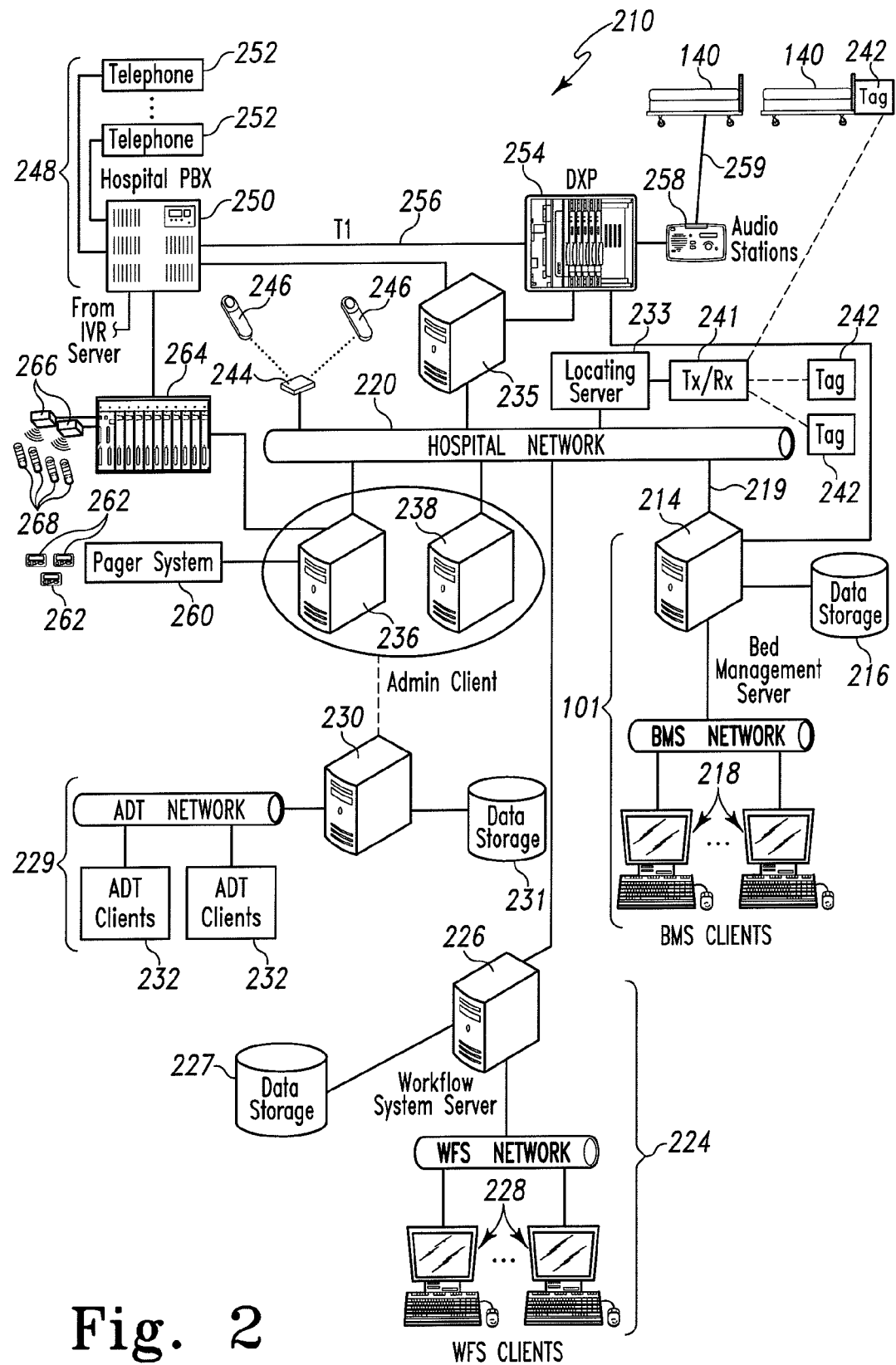
FIG. 2 is block diagram of a network of the healthcare facility which is utilized by the bed management system.

The healthcare facility 110 may include a network which supports bed management as well as other patient workflow tasks. An embodiment of such a network 210 is depicted in FIG. 2. The network 210 includes the bed management system 101 having a bed management system (BMS) server 214, data storage device 216, and associated BMS clients 218. As explained in detail below in regard to FIG. 3, the bed management system 101 in an embodiment assigns beds 140 to patients 130 based upon healthcare attributes of the patients 130 and capabilities of the beds 140. BMS server 214 is coupled to hospital network infrastructure 220 via a wired or wireless communication link 219. The architecture of network 210 is generally at the discretion of information technology personnel of the healthcare facility 110 and may include additional pieces of hardware (not shown) such as routers, backup power systems, and medical equipment, such as patient monitors, hospital beds, X-ray systems, and so on having networking capability.

In the illustrative example, the network 210 further includes a workflow system 224. The workflow system 224 includes a workflow system (WFS) server 226, a data storage device 227, and one or more WFS clients 228. The workflow system 224 manages patient workflow through the healthcare facility 110. To this end, the workflow system 224 may assign tasks to medical staff and track and record the completion of such assigned tasks. Furthermore, the workflow system 224 may maintain patient data such as electronic medical records for patients 130. The electronic medical record of the patient data includes information regarding medical conditions of the patients 130. In one embodiment, caregivers enter diagnosis codes into the workflow system 224 via client devices such as WFS clients 228. The diagnosis codes provide information regarding the condition of the patient. The World Health Organization (WHO) has published an *International Statistical Classification of Diseases and Related Health Problems* which is commonly abbreviated as ICD. The ICD provides a detailed description of known diseases and injuries along with their diagnoses and unique diagnosis codes of up to six characters. Healthcare facilities in the United States tend to use ICD-9-CM codes which is the ninth revision of the ICD with a clinical modification that includes the standard ICD-9 codes as well as additional codes that identify specific health interventions and procedures taken or to be taken by medical professionals.

The network 210 also includes an admissions, discharge, and transfer (ADT) system 229 which includes an ADT server 230, a data storage device 231, and one or more ADT clients 232. Network 210 further includes a locating server 233, a first communication system server 235, a second communication system server 236, and a plurality of additional servers 238. Illustratively, only a single additional server 238 is shown, but server 238 is intended to be representative of all of the other servers that are included in network 210. Each of the various servers 214, 226, 230, 232, 233, 235, 236, 238 has a processor (not shown) for executing associated application software. For example, BMS server 214 and BMS clients 218 execute bed management software to provide bed management features such as assigning patients 130 to beds 140.

Locating server 233 executes software to track the whereabouts of equipment, beds, patients and/or other persons such as medical staff throughout the associated healthcare facility 110 based on wireless signals received by units 241 from tags 242. In some embodiments, units 241 periodically transmit a wireless query within a limited area of the healthcare facility 110 and any tags 242 within the limited area respond by transmitting unique identification (ID) data which is received by an associated unit 241 and forwarded to locating server 233. Locating server 233 associates the unique ID data from the tags 242 with ID data, such as a serial number, of the corresponding unit 241 which receives the wireless transmission from the tags 242. During execution of the bed management software by the BMS server 214 or the workflow software by WFS server 226, if there is a need for data relating to the location of any equipment, beds, or persons being tracked by the locating-and-tracking software being executed by locating server 233, then server 214 or 226 respectively sends a query to locating server 233 and locating server 233 responds with the requested information, if it is available. Alternatively, locating server 233 may periodically update servers 214, 226 with some or all of the data corresponding to the whereabouts of the equipment, beds and persons being tracked and servers 214, 226 may store such data in the associated data storage devices 216, 227 for possible future use.

Communication system server 235 executes application software to send and receive communication data to/from one or more communication units 244 which, in turn, communicate wirelessly with portable wireless communication devices 246 carried by persons on the medical staff. In the illustrative example, communication system server 235, units 244, and devices 246 are configured to support voice communications between users of devices 246 and the other portions of the network 210. Communication system server 235 determines what other portion of network 210 users of devices 246 are intending to communicate with and transmits data representative of the voice communications to that portion of network 210. For example, the healthcare systems standard telephone system includes one or more private branch exchanges (PBX's) 250 and a plurality of telephones 252. Communication system server 235 is coupled to the one or more PBX's 250 to communicate therewith. Network 210 also includes one or more Digital Phone Switch (DXP) units 254 that are coupled to the PBX's via associated T1 lines 256. A plurality of audio stations 258 are located throughout the healthcare facility 110, typically in patient rooms, and are also coupled the DXP units 254. Thus, users of portable wireless communication devices 246 can speak to and hear from users of telephones 252 and users of audio stations 258.

Besides providing audio communications, the audio stations 258 in an embodiment further provide an interface between medical equipment such as beds 140 and the network 210. In particular, beds 140 may be coupled to an audio station 258 via a wired connection 259. The wired connection 259 enables a bed 140 to provide the network 210 with information regarding capabilities of the bed 140 as well as bed status information such as head angle, side rail positions, etc. The wired connection 259 may further associate the bed 140 with the audio station 258. Since the workflow system 224 in an embodiment knows which room/area each audio station 258 is located, associating a bed 140 with an audio station 258 informs the workflow system 224 that the respective bed 140 is in the same room/location as the audio station 258 to which it is attached. The bed management system 101, workflow system 224 and other network systems and servers may receive the bed capabilities, bed status, and location information from the beds 140 via network 210 and may update respective memory structures and/or data storage devices 216, 227, 231 accordingly. Some embodiments may further support tagging beds 140 with tags 242 or otherwise incorporating wireless tag capabilities into beds 140 so the network 210 may receive bed capabilities, bed status, location data, and/or other information regarding beds 140 via location sensors 241 and provide such received information to interested network systems and servers.

As mentioned, the beds 140 may provided information regarding bed capabilities to the network 210. The beds 140 may include various capabilities that are generally beneficial to patients 130 having certain medical conditions. Such capabilities include but are not limited to full-chair patient position mechanism that places the bed 140 into a chair position at a touch of a button; a head of bed alarm that generates an alarm or alert when the head of bed is lowered below a certain angle (e.g. 30 degrees); continuous lateral rotation, percussion, and/or vibration therapies, retractable foot mechanisms which enable customizing the overall length of the bed; integrated scales which enable weighing a patient in the bed; turn assists mechanisms which aid a caregiver in turning a patient in the bed; and full-body zoned pressure-relief air surfaces to aid in preventing pressure ulcers related to immobility, to name a few. The beds 140 may indicate whether they include one or more of these capabilities in order aid assignment of appropriate beds 140 to patients 130.

In one embodiment, communication system devices 246 and units 244 are the type marketed by Vocera Communications, Inc. of Cupertino, Calif. and sold under the Vocera™ brand name. Such Vocera™ devices 246 (referred to sometimes as badges) may be worn by users in the same manner as tags 242 described above. The Vocera™ badges 246 and Vocera™ units 244 communicate over an 802.11b LAN infrastructure and also with the PBX's 250 via communication system server 235 which executes associated Vocera™ server software. Communication system devices 246 and units 244 which communicate according to wireless communications protocols other than 802.11b, such as the Bluetooth protocol, for example, are contemplated by this disclosure.

Illustrative network 210 also includes a pager system 260 which is coupled to communication system server 236 and which includes a plurality of pagers 262 carried by some of the medical staff. Also coupled to communication system server 236 and to PBX's 250 are one or more master control units 264 of a dedicated wireless telephone system of the healthcare facility. The dedicated wireless telephone system further includes a number of base stations 266 and number of wireless telephone handsets 268. As was the case with Vocera™ badges 246, handsets 268 are considered to be portable wireless communication devices according to this disclosure. While it is within the scope of this disclosure for network 210 to have any type of dedicated wireless telephone system, or none at all, in one embodiment, master control units 264, base stations 266, and handsets 268 are of the type marketed by Spectralink Corporation of Boulder, Colo. and/or ASCOM Ltd. of Berne, Switzerland. The Spectralink™ base stations 266 and handsets 268 communicate wirelessly via a scheme of frequency hopping spread spectrum over four TDMA channels in the 902-928 MHz radio frequency range. The Spectralink™ master control units 264 communicate with the PBX's 250 of system 210 either via a digital and/or an analog interface.

In accordance with this disclosure, the application software on servers of network 210 may be placed on other servers such that one or more of servers may be omitted from network 210. Thus, to give one example, the bed management software on BMS server 214 may instead reside on the WFS server 226 along with the workflow software. In some embodiments, the bed management software and the workflow software may be combined into a single software package. In addition, data storage device 216 may be included as part of the memory of BMS server 214 or as part of the memory of another server (not shown). In some embodiments, data storage devices 216, 227, 231 may include other types of storage devices such as floppy or removable disk drives, a direct access storage device (DASD), a hard disk drive, a CD drive, a DVD drive, a tape drive, and the like that are included in, associated with, or coupled to servers 214, 226, 230 and that read data stored on the corresponding type of data storage media (e.g. floppy disk, CD, DVD, tape, memory chip, etc.). Thus, systems 101, 224, 229 may comprise multiple storage devices that are networked together and networked to servers 214, 226, 230 as well as comprising a portion of the memory of servers 214, 226, 230.

Furthermore, the various portions of network 210 which interact may be grouped together in any logical fashion and considered to be one system, with some portions of network 210 being considered subsystems of the designated system. Thus, servers 233, 235, 236, units 244, 264, and devices 244, 246 may be considered part of workflow system 224 with some of these servers, units, and devices being grouped into subsystems.

Figure 3:
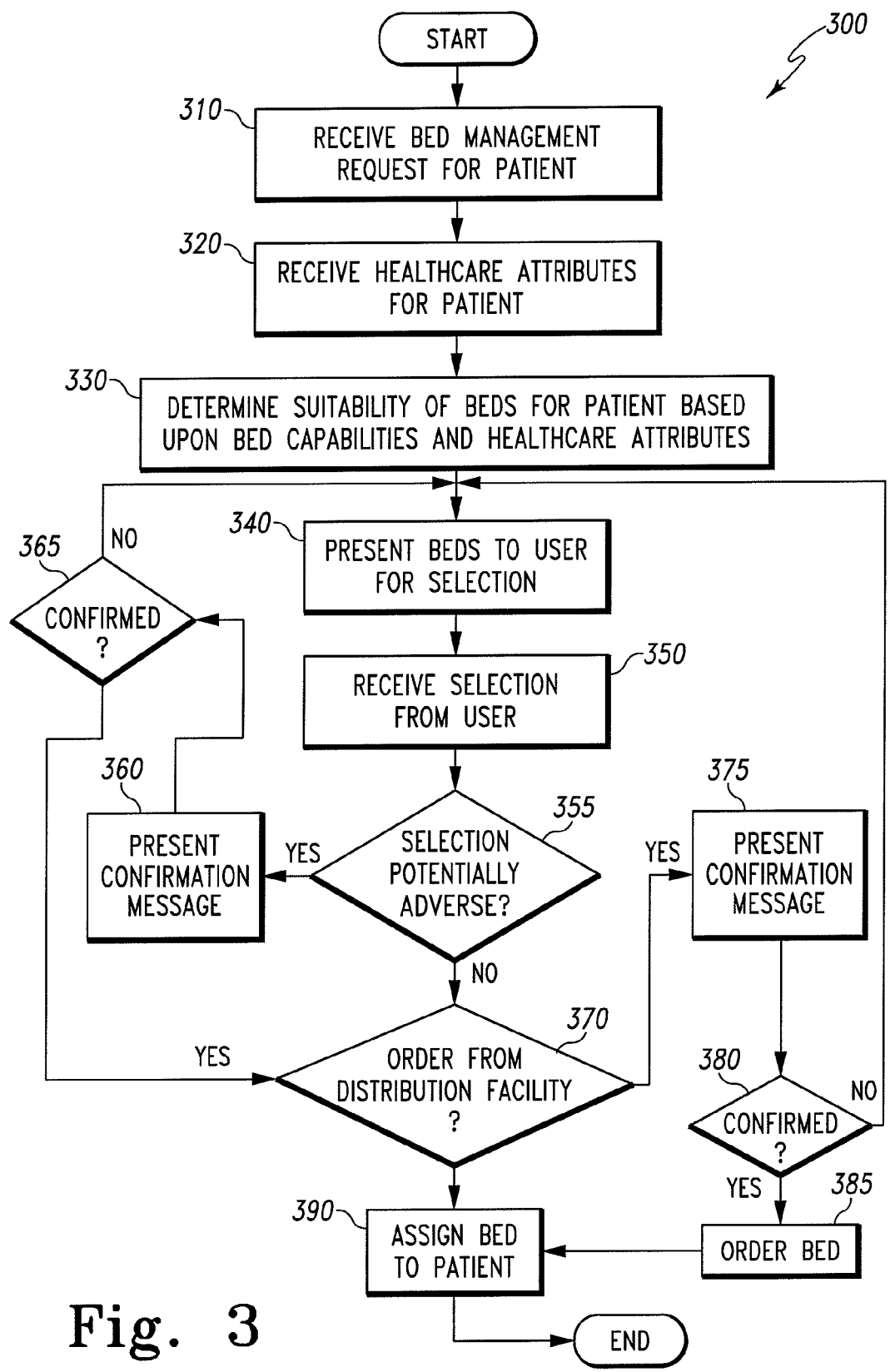
FIG. 3 is a flow diagram showing an example of an algorithm for managing bed assignments based upon bed capabilities and healthcare attributes of patients.

A method 300 for processing a bed management request implemented by the bed management system 101 is illustrated in FIG. 3. In block 310, the bed management system 101 receives a bed management request for a patient 130. A bed management request may be generated in response to various events. For example, a bed management request may be generated by the ADT system 229 in response to a patient 130 being admitted so that a bed 140 is assigned to the patient 130. A bed management request may also be generated by the ADT system 229 in response to a patient 130 being discharged so that the bed 140 assigned to the discharged patient 130 is returned to the inventory of available beds. Further, the ADT system 229 may generate a bed management request in response to a patient 130 being transferred from one location to another so that currently assigned bed 140 may be returned to the inventory of available beds and a new bed 140 may be assigned to the patient 130. Bed management requests may also be generated in response to medical staff requesting a bed 140 for a patient 130 via clients of the network 210 such as the BMS client 218 or the WFS client 228. Bed management requests may be generated in response to events other than those listed above. As such, the above are merely illustrative and other manners of generating bed management requests are contemplated by the present disclosure.

As depicted, the bed management system 101 in block 320 may receive healthcare attributes for the patient 130 who is the subject of the received bed management request. The bed management system 101 may receive the healthcare attributes for the patient 130 as part of the bed management request. If not received as part of the bed management request, the bed management system 101 may request the healthcare attributes for the patient 130 from the network 210. The bed management system 101 may request patient data such as the electronic medical record for the patient 140 from the workflow system 224 and/or another system of the network 210. As mentioned above, the electronic medical record includes healthcare codes such as, for example, ICD-9-CM diagnosis and procedure codes which provide information regarding physical health conditions, mental health conditions, procedures performed, and/or procedures to be preformed. Moreover, the electronic medical record may include other healthcare attributes for the patient 130 such as, for example, the patient's weight, the patient's height and the patient's age that otherwise may not be discernible from the healthcare codes of the electronic medical record.

In block 330, the bed management system 101 may determine suitability of available beds 140 for the patient 130. In an embodiment, the bed management system 101 may determine suitability by taking into account capabilities of the beds 140 and attributes of the patient 130. At a high level, the bed management system 101 searches amongst the inventory of beds 140 maintained by the healthcare facility 110 and/or beds that can be ordered from the bed distribution facility 120 and ranks the beds 140 based upon how well the capabilities of the bed 140 meet the healthcare needs of the patient 130. The bed management system 1010 may utilize a number of different algorithms to implement ranking or otherwise determining the suitability of the beds for a particular patient. For example, the bed management system 101 may utilize linear programming and/or other optimization techniques to implement its bed assignment logic. To support such techniques, cost or benefit values may be associated or otherwise assigned to bed models or bed capabilities based upon how the bed models or bed capabilities relate to patient attributes. The bed management system 101 may then determine a ranking or suitability score for each bed 140 on a per patient 130 basis based upon the cost/benefit values associated with the bed 140 in regard to the healthcare attributes of the patient 130.

A person or persons knowledgeable about the beds 140 and how their capabilities relate to healthcare attributes may assign or otherwise associate a costs/benefit value to each bed capability and/or bed model on a per healthcare attribute basis. The bed management system 101 may further utilize various artificial intelligence or learning algorithms to evolve or otherwise generate the cost/benefit values for the bed capabilities in regard to the healthcare attributes. For example, the bed management system 101 may be placed in a training mode in which a training data set is applied to the bed management system 101 in order to configure the bed management system 101. The bed management system 101 may further update such cost/benefit values based upon real-time bed allocation data. For example, the bed management system 101 may rank a first bed as the "best fit" or "most suitable" for a patient; however, medical staff may override or ignore the bed identified by the bed management system 101 and chose another bed 140 for the patient 130. The bed management system 101 may utilize such corrective feedback to improve the accuracy of future bed assignments.

The bed management system 101 may take many factors into consideration when determining suitability of beds 140 for a patient 130. In particular, the bed management system 101 may favor beds 140 having capabilities that are beneficial or otherwise address one or more healthcare attributes of the patient 140. For example, a bed 140 with a continuous lateral rotation therapy (CLRT) capability may be helpful for a patient 130 at risk of pulmonary complications. Thus, the bed assignment logic may be implemented to favor a bed 140 with CLRT capabilities for a patient 130 that is identified as having pulmonary issues or is at risk of pulmonary complications based upon healthcare attributes obtained from the electronic medical record for the patient 130. Conversely, activation of CLRT capabilities of a bed 140 may adversely effect a patient 130 in traction given the desirability of keep the patient 130 immobile. Thus, the bed management system 101 may be implemented to bias against a bed with CLRT capabilities for a patient 130 to be placed in traction based upon healthcare attributes obtained from the electronic medical record for the patient 130.

Besides taking into account the suitability of a bed capability for one or more healthcare attributes of a patient, the bed management system 101 may further take into account whether a bed 140 is part of the current inventory of the healthcare facility 110 or whether the bed 140 needs to be ordered from a bed distribution facility 120. Since the healthcare facility 110 is likely to incur additional costs for a bed 140 that is ordered from the bed distribution facility 120, the bed management system 101 in one embodiment is configured to favor a bed 140 that is in current inventory over a bed 140 that must be ordered from the bed distribution facility 120.

Those skilled in the art should appreciate that the bed management system 101 may implement ranking functionality in various manners. Further, the ranking functionality may weight more heavily or more strongly favor some criteria than others. The manner by which the bed management system 101 ranks the suitability of the beds 140 for a particular patient 130 may vary greatly based upon policies and procedures of the healthcare facility 110 in question. As a result, there may not be "one" bed ranking algorithm that is appropriate or best for all healthcare facilities. The present disclosure contemplates customizing and tuning the ranking aspects of the bed management system 101 per needs of the healthcare facility 110 in which deployed.

Moreover, to enable quicker ranking of the beds 140, the bed management system 101 in an embodiment places each bed 140 in a corresponding class. For example, a healthcare facility 110 may have fifty beds 140 with identical capabilities (e.g. same bed model with the same optional capabilities). Instead of ranking each of these fifty beds individually, the bed management system 101 may group them into a single bed class and rank the class. In this manner, the bed management system 140 may simply rank the possibly ten different classes of beds the healthcare facility 110 has at its disposal instead of separately ranking each of the possibly hundreds of beds of the healthcare facility 110.

The bed management system 101 may then present a user with one or more beds 140 (block 340). In one embodiment, the bed management system 101 may provide a list of the top ranked beds 140 via a display of one of the BMS clients 218. The bed management system 101 may display the list of beds in an order where higher ranked beds are listed first followed by lower ranked beds. The bed management system 101 may further present the bed ranking and/or suitability score in order to provide a user with further details regarding how well the bed meets the needs of a particular patient based upon the ranking criteria of the bed management system 101. As discussed above, the bed management system 101 may group like beds 140 together instead of ranking them separately. Similarly, the bed management system 101 may present the user with only one bed 140 of each bed class so that the beds 140 presented to the user are not all of the same bed class.

In block 350, the bed management system 101 may receive a selection from the user that identifies the bed 140 of the list of presented beds 140 that is to be assigned to the patient 130. The user may provide the selection using an input device such as a mouse and selecting, via a double-click or some other gesture, the bed 140 to be assigned. In one embodiment, the bed management system 101 provides the user with an option to display additional beds 140 in case the user is not satisfied with any of the choices presented. In such an embodiment, the bed management system 101 may simply list additional lower ranked beds 140. The bed management system 101 may further provide the user with an option to list all available beds or even all beds of the facility if still dissatisfied with the choices presented by the bed management system 101. In this manner, the bed management system 101 aids the user in assigning a bed 140 to a patient 130 but still enables the user to assign any bed 140 of the healthcare facility 110 to the patient 130 regardless of the rank the bed management system 101 assigned to the bed 140.

In response to the selection, the bed management system 101 in block 355 determines whether the selected bed 140 has one or more capabilities that is potentially adverse to one or more healthcare attributes of the patient 130. In one embodiment, the bed management system 101 may maintain a database or other data structure that relates healthcare codes to bed capabilities that are adverse to health conditions indicated by the healthcare code. Based on this information, the bed management system 101 may determine that the selected bed 140 has capabilities that are potentially adverse or unsuitable for the patient 130. In response to determining the selected bed 140 is potentially unsuitable for the patient 130, the bed management system 130 may present the user with a confirmation message requesting confirmation for the bed selection in block 360. As part of the confirmation message, the bed management system 130 may identify why the selected bed 140 may be unsuitable for the patient 130. The bed management system 130 may further provide the user with an option to request additional information regarding the selected bed 140 and/or healthcare attributes of the patient 130.

If the bed management system 101 determines in block 365 that the user did not confirm the bed selection, the bed management system 101 may return to block 340 in order to present the user again with the list of ranked beds. Otherwise, the bed management system 101 in block 370 determines whether the selected bed 140 is to be ordered from the bed distribution facility 120. In response to determining the selected bed 140 is to be ordered from the bed distribution facility 120, the bed management system 130 may present the user with a confirmation message requesting confirmation for ordering the selected bed 140 in block 375. As part of the confirmation message, the bed management system 130 may identify the cost associated with ordering the selected bed 140 as well as other details regarding the bed 140 or order process such as estimated delivery time. The bed management system 130 may further provide the user with an option to request additional information regarding the selected bed 140 and/or the order process.

If the bed management system 101 determines in block 380 that the user did not confirm the bed selection, the bed management system 101 may return to block 340 in order to present the user again with the list of ranked beds. Otherwise, the bed management system 101 in block 385 may order the selected bed 140 or aid the user in ordering the selected bed 140. To this end, the bed management system 101 may provide the user with instructions for manually contacting the bed distribution facility 120 and ordering the selected bed 140. For example, the bed management system 101 may provide the user with telephone numbers, contact names, account numbers, bed model numbers, and like to enable the user to call the bed distribution facility 120 and place the order. The bed management system 101 may support automated order schemes as well such as, for example, automatically generating and sending an e-mail message that requests the selected bed 140 from the bed distribution facility 120, or connecting to a procurement server of bed distribution facility 120 and placing an order.

In block 390, the bed management system 101 may assign the bed 140 identified by the received selection to the patient 130. Accordingly, the bed management system 101 updates records maintained by the bed management system 101. The bed management system 101 may further refine its ranking algorithm based upon the selection especially if the selected bed 140 was not the top ranked bed 140. To this end, the bed management system 101 may adjust one or more weights or benefit/cost values used by the bed management system 101 to arrive at its ranking. The bed management system 101 may further inform other systems of the network 210 to indicate that the selected bed 140 is being assigned to the patient 130. By informing other systems of the network 210, other systems may take actions in response to the assignment. For example, the workflow system 228 may assign as person, in response to the bed assignment, to transport the patient 130 to the assigned bed 140 or the assigned bed 140 to the patient 130.

While bed management has been described above in regard to FIG. 3 as a semi-automated method wherein a user selects a bed from a list of ranked beds, other embodiments may automate one or more of the user actions. For example, the bed management system 101 may be configured to assign the top ranked bed to a patient without requesting user selection. Furthermore, the bed management system 101 may be configured to automatically order a bed from the bed distribution facility 120 without first requesting confirmation from a user. Other modifications regarding automation and user confirmation are contemplated by the present disclosure.

Figure 4:
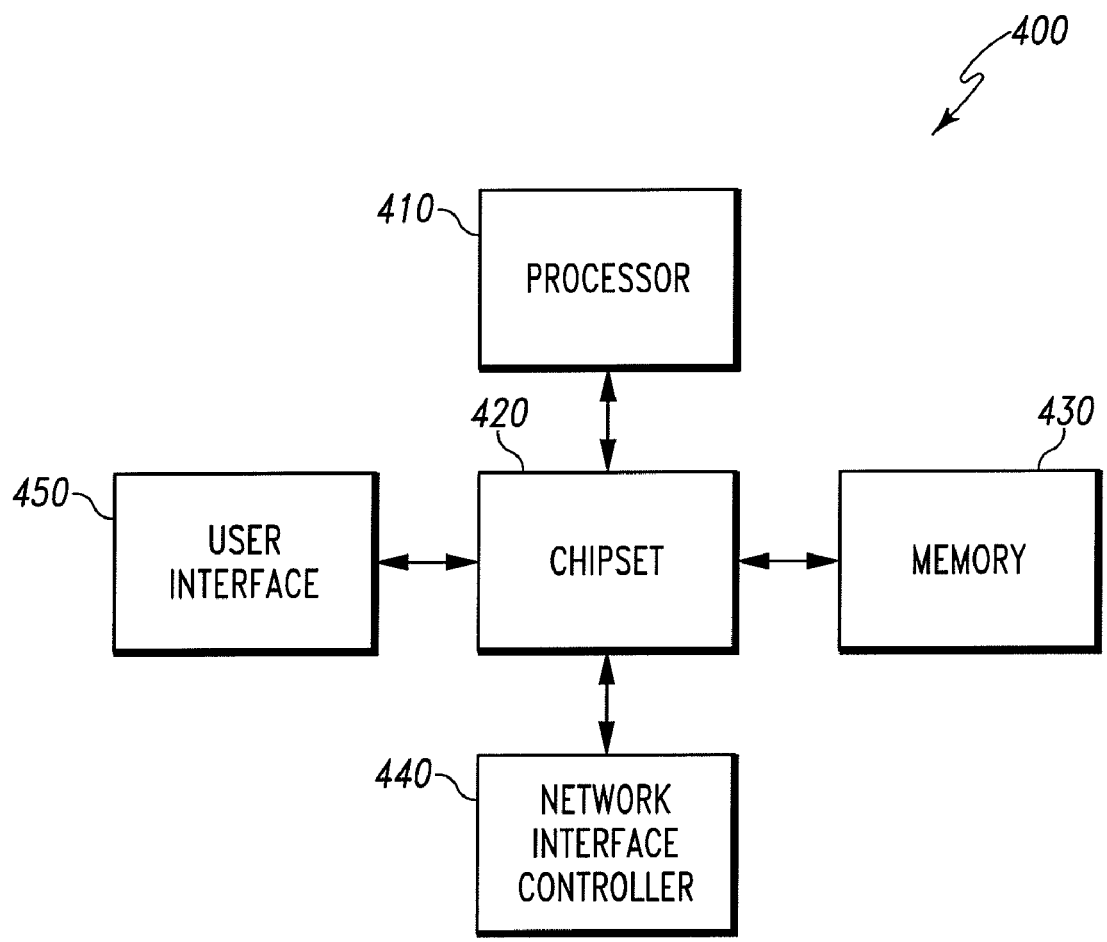
FIG. 4 is a block diagram depicting a computing device that may be used to implement servers and/or clients of the network depicted in FIG. 2.

Referring now to FIG. 4, a general block diagram of a computing device 400 such as servers 214, 226, 230, 233, 235, 236, 238 and clients 218, 228 is depicted. The computing device 400 comprises one or more processors 410. The processors 410 may perform actions in response to executing instructions. For example, the processors 410 may perform bed management functions and/or patient workflow functions in response to executing instructions of a machine-readable medium. The processor 410 may be implement using general purpose processors such as the server, desktop and laptop processors marketed by Intel Corporation, Advance Micro Devices (AMD), Incorporated, and International Business Machines Corporation. The processor 410 may further be implemented using a microcontroller, field programmable array, an application specific integrated circuit (ASIC), and/or other integrated circuit capable of being programmed or otherwise configured to perform the tasks described herein.

The computing device 400 further comprises a chipset 420. The chipset 420 may comprise one or more integrated circuit packages or chips that operatively couple the processors 410 to memory 430, network interface controller 440, and a user interface 450. To this end, the chipset 106 may comprise interfaces and controllers such as peripheral component interconnect (PCI) interfaces, accelerated graphics port (AGP) interfaces, universal serial bus (USB) controllers, memory controllers, disk controllers, and the like to interconnect components of the computing device 400. The above identified interconnect technologies are illustrative and other interconnect technologies, in addition to or alternative to the above, are also contemplated by the present disclosure.

The memory 430 of the computing device 400 comprises memory devices having addressable storage locations that processor 410 may read data from and/or write data to. The memory 430 may comprise one or more different types of memory devices such as, for example, dynamic random access memory (DRAM) devices, synchronous dynamic random access memory (SDRAM) devices, double data rate (DDR) SDRAM devices, quad data rate (QDR) SDRAM devices, or other volatile or non-volatile memory devices. The above identified memory technologies are illustrative and other memory technologies, in addition to or alternative to the above, are also contemplated by the present disclosure.

The network interface controller 440 of the computing device 400 operatively couples the computing device 400 with the network 210. The network interface controller 440 may implement various wired and/or wireless technologies such as, for example, a wired LAN (local area network)

interface (e.g. IEEE 802.3 which is also known as Ethernet), a wireless LAN interface (e.g. IEEE 802.11a, b, g, and/or n variants which are also known as Wi-Fi), a wireless WAN (wide area network) interface (e.g. IEEE 802.16 which is also known as WiMAX), and/or an infrared interface (e.g. IEEE 802.15.1 which is also known as Bluetooth). By operatively coupling the computing device 400 with the network 210, the network interface controller 440 enables the computing device 400 to send and receive data to and from other devices of the network 210. Moreover, the network interface controller 440 may permit servers such as servers 214, 226, 230 to be implemented as headless servers without a user interface 450 and receive user requests and present users with information via the network interface controller 440 and client devices of the network 210 such as client devices 218, 228, 240. The above identified networking technologies are illustrative and other networking technologies, in addition to or alternative to the above, are also contemplated by the present disclosure.

The user interface 450 presents the user with information and enables a user to input data and make selections based upon the information presented. To this end, the user interface 450 may comprise one or more input and/or output devices such as, for example, a keyboard, a mouse, a CRT (cathode ray tub) monitor, flat panel display, and/or printer to receive user input and output or present information to the user. The above identified input/output devices of the user interface 450 are illustrative and other input/output devices, in addition to or alternative to the above, are also contemplated by the present disclosure.

While certain features of the invention have been described with reference to various embodiments, the description is not intended to be construed in a limiting sense. Various modifications of the described embodiments, as well as other embodiments of the invention, which are apparent to persons skilled in the art to which the invention pertains are deemed to lie within the spirit and scope of the invention.

What is claimed is:

1. A machine readable medium for managing beds at a healthcare facility, the machine readable medium being non-transitory and comprising a plurality of instructions that, in response to being executed, results in a computing device:
   receiving patient data that identifies a plurality of medical conditions of a patient,
   identifying one or more beds that address a medical condition of the plurality of healthcare medical conditions,
   ranking the one or more beds based on suitability for the one or more medical conditions of the patient, wherein the ranking further comprises the computing device ranking unassigned beds of the healthcare facility and of a bed distribution facility that is remote from the healthcare facility, based upon suitability of the unassigned beds for the plurality of medical conditions identified by the patient data,
   presenting the one or more beds to a user, the user being a person other than the patient,
   receiving a selection from the user that identifies the bed of the one or more beds to be assigned to the patient,
   indicating to the user that the selection is potentially adverse to the patient and permitting the user to confirm the selection,
   assigning a bed to the patient based upon the plurality of medical conditions of the patient identified by the patient data and a capability of the bed, and
   when there is no bed at the healthcare facility suitable having capabilities for the patient, receiving a selection from the user that identifies a bed of the bed distribution facility as the bed to be assigned to the patient,
   placing an order to the remote bed distribution facility for a bed that has suitable capabilities for addressing one or more medical conditions of the patient.

2. The machine readable medium of claim 1, wherein the plurality of instructions, in response to being executed, further result in the computing device
   selecting the bed assigned to the patient based upon at least one medical condition of the plurality medical conditions identified by the patient data.

3. The machine readable medium of claim 1, wherein the plurality of instructions, in response to being executed, further result in the computing device
   identifying one or more unassigned beds with a capability that addresses at least one medical condition of the patient as identified by the patient data.

4. The machine readable medium of claim 1, wherein the plurality of instructions, in response to being executed, further result in the computing device
   ranking unassigned beds based upon whether capabilities of the unassigned beds are suitable for the plurality of medical conditions identified by the patient data,
   presenting a ranking of one or more beds of the unassigned beds to a user, and
   receiving a selection from the user that identifies the bed of the one or more beds to be assigned to the patient.

5. The machine readable medium of claim 1, wherein the plurality of instructions, in response to being executed, further result in the computing device
   defining bed classes based upon bed capabilities,
   ranking bed classes based upon suitability of beds of the bed classes for the plurality of medical conditions identified by the patient data, and
   receiving a selection from the user that identifies a bed of one of the bed classes as the bed to be assigned to the patient.

6. The machine readable medium of claim 1, wherein the patient data comprises a healthcare code that identifies a medical condition as one of the medical conditions of the patient.

7. The machine readable medium of claim 1, wherein the patient data comprises a healthcare code that identifies a medical procedure as one of the medical conditions of the patient.

8. The machine readable medium of claim 1, wherein the plurality of instructions, in response to being executed, further result in the computing device
   receiving a request to assign a bed to the patient, and
   assigning the bed to the patient in response to the request if the request is not adverse to the patient.

9. A computer-implemented method of managing beds at a healthcare facility, the computer-implemented method comprising:
   determining with a computer device suitability of a plurality of beds for a patient based upon capabilities of the beds stored in memory associated with the computer device and a plurality of medical conditions of the patient received by the computer device,
   identifying one or more beds that address a medical condition of the plurality of healthcare medical conditions,
   ranking the one or more identified beds based on suitability for the one or more medical conditions of the patient, wherein the ranking further comprises the computing device ranking unassigned beds of the healthcare facility and of a bed distribution facility that is remote from the healthcare facility, based upon suitability of the unassigned beds for the plurality of medical conditions identified by the patient data, presenting the one or more beds to a user, the user being a person other than the patient, receiving a selection from the user that identifies the bed of the one or more beds to be assigned to the patient, indicating to the user that the selection is potentially adverse to the patient and permitting the user to confirm the selection, assigning with the computer device a bed of the plurality of beds to the patient based upon suitability of the bed for the patient as determined by the computer device, and when there is no bed at the healthcare facility having suitable capabilities for the patient, receiving a selection from the user that identifies a bed of the bed distribution facility as the bed to be assigned to the patient, placing an order with the computer device to the remote bed distribution facility for a bed that has suitable capabilities for addressing one or more medical conditions of the patient.

10. The computer-implemented method of claim 9, further comprising retrieving a medical record for the patient, identifying the plurality of medical conditions from the medical record, presenting the plurality of beds to a user based upon suitability of the plurality of beds, and assigning the bed to the patient based upon a user selection that identifies the bed from the plurality of beds if the selection is not adverse to the patient.

* * * * *

UNITED STATES PATENT AND TRADEMARK OFFICE
CERTIFICATE OF CORRECTION

| | | |
|---|---|---|
| PATENT NO. | : 8,280,748 B2 | Page 1 of 1 |
| APPLICATION NO. | : 11/869069 | |
| DATED | : October 2, 2012 | |
| INVENTOR(S) | : Allen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 697 days.

Signed and Sealed this
Twenty-sixth Day of August, 2014

Michelle K. Lee
*Deputy Director of the United States Patent and Trademark Office*